(12) United States Patent
Myers

(10) Patent No.: US 6,960,175 B1
(45) Date of Patent: Nov. 1, 2005

(54) ORTHOPEDIC LEG BRACE

(75) Inventor: William Neill Myers, Huntsville, AL (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 140 days.

(21) Appl. No.: 10/652,087

(22) Filed: Aug. 22, 2003

(51) Int. Cl.$^7$ .................................................. A61F 5/00
(52) U.S. Cl. .............................. 602/16; 602/23; 602/26
(58) Field of Search ................................ 602/5, 16, 23, 602/26; 623/39–44; 16/324–326

(56) References Cited

U.S. PATENT DOCUMENTS

| | | | |
|---|---|---|---|
| 2,943,622 A | 7/1960 | Nelson | |
| 4,179,759 A | 12/1979 | Smith | |
| 4,433,679 A | 2/1984 | Mauldin et al. | |
| 4,451,939 A | * | 6/1984 | Thompson ................... 623/40 |
| 4,520,804 A | 6/1985 | DiGeorge | |
| 4,632,096 A | 12/1986 | Harris | |
| 4,688,559 A | 8/1987 | Vito et al. | |
| 4,791,916 A | 12/1988 | Paez | |
| 5,490,831 A | 2/1996 | Myers et al. | |
| 5,776,086 A | 7/1998 | Pansiera | |
| 5,899,869 A | 5/1999 | Barrack, Jr. et al. | |
| 6,001,075 A | 12/1999 | Clemens et al. | |
| 6,527,733 B1 | 3/2003 | Ceriani et al. | |
| 6,635,024 B2 | * | 10/2003 | Hatton et al. ................. 602/16 |
| 6,770,045 B2 | * | 8/2004 | Naft et al. .................... 602/16 |
| 2002/0169402 A1 | 11/2002 | Hatton et al. | |

* cited by examiner

Primary Examiner—Henry Bennett
Assistant Examiner—Amanda Wieker
(74) Attorney, Agent, or Firm—James J. McGroary; Norman L. Wilson, Jr.

(57) ABSTRACT

Knee braces generally have been rigid in both the knee bending direction and in the knee straightening direction unless a manually operated release is incorporated in them to allow the knee to bend. Desirably a braced knee joint should effectively duplicate the compound, complex, actions of a normal knee. The key to knee braces is the knee joint housing. The housing herein carries a number of cam action pawls, with teeth adapted to engage the internal teeth of a ratchet ring mounted in the housing. Cam action return springs and the shape of the cam action pawl teeth allow rotation of the ratchet ring in a leg straightening direction while still supporting a load. The leg can then be extended during walking while at the same time being prevented by the cam action pawls from buckling in the knee bending direction.

4 Claims, 3 Drawing Sheets

ORTHOPEDIC LEG BRACE

STATEMENT REGARDING FEDERALLY SPONSORED RESEARCH AND DEVELOPMENT

The invention described in this patent was made by an employee of the United States Government and may be manufactured and used by or for the Government for governmental purposes without the payment of any royalties.

CROSS-REFERENCES TO RELATED APPLICATIONS

There are no applications related to this application.

FIELD OF THE INVENTION

This invention relates to orthopedic leg braces, especially those which brace the upper and lower portions of a user's leg and which incorporate a knee joint assembly between the upper and lower braces.

BACKGROUND OF THE INVENTION

There is a long-standing need for leg braces for knees impaired by temporary or permanent loss of neuromuscular control or by loss of control of a knee joint through a knee injury. For stability or bracing, such knee braces must have stays or brace members secured firmly to the leg both below and above the knee with a knee joint housing between the brace members.

It is generally realized, as is discussed in the Lewis et al. U.S. Pat. No. 4,361,142, that it is particularly difficult to provide orthopedic knee appliances which provide stability while still duplicating or accommodating the complex flexion and extension actions which a knee undergoes. At the same time the braced knee joint must effectively duplicate the compound, complex, actions of a normal knee. Otherwise the knee brace may well be injurious to the user.

A study of the prior art shows that duplication of normal knee actions has not been fully accomplished. Thus knee braces generally have been rigid in both the knee bending direction and in the knee straightening direction unless a manually operated release is incorporated in them. As one example a double-locking ratchet knee joint, pivotally connected between the upper and lower leg, is described in U.S. Pat. No. 4,520,804. Relative pivotal movement between the knee joint and upper and lower leg sections is achieved manually by a pair of actuatable locking levers. Rotary movement of the ratchet wheel is effected only by manual rotation of a locking pawl control lever. Presently, then, it is not possible to straighten the leg as in normal walking, especially for traveling up steps.

An object of this invention is to provide a knee brace allowing a leg bent at the knee to be straightened while at the same time being prevented from buckling in the knee bending direction.

Another object of the invention is the provision of a knee brace which is releasable so that it can free wheel in both directions when it is not in use, that is, under a no load condition.

Still another object is to provide a knee brace which will lock in any position because its locking mechanism functions in small increments.

Existing knee brace locking devices have been either cone clutches, roller type clutches or single pawl ratchet devices. Variations in friction due to clutch surface conditions, as well as the distance pawls must normally travel before engaging or locking, can lead to a knee joint which gives way. My issued patent, U.S. Pat. No. 5,490,831 overcame many of these disadvantages, but as noted in the prior art, there is still room for improvement. This invention embraces a major step in that direction.

SUMMARY OF THE INVENTION

Orthopedic knee brace assemblies usually include upper and lower side braces to support a user's leg with a knee joint housing between them accommodating means for pivotal movement. The key to knee braces, then, is the knee joint housing. The knee joint housing herein is in the form of inner and outer housing members. The upper side brace is integral with the outer housing member, and the lower side brace is integral with the inner housing member. A ratchet ring having internal teeth is mounted in the outer housing member so that it rotates when the upper side brace swivels. A number of cam action pawls, with teeth adapted to engage the internal ratchet ring teeth, are mounted in the inner housing member. The cam action pawls are provided with return springs to hold the pawl teeth in engagement with the ratchet ring teeth. The inner and outer housing members are coupled together to form a knee joint hinge. Ratchets are created in the housing when the cam action pawls in the inner housing member engage the teeth inside the ratchet ring in the outer housing member. A control mechanism moves the cam action pawls into and out of a locking engagement with the ratchet ring teeth. Cam action return springs and the shape of the cam action pawl teeth allow rotation of the ratchet ring in a leg straightening direction while still supporting a load. The leg can then be extended during walking while at the same time being prevented by the cam action pawls from buckling in the knee bending direction. An actuating rod acts on the control mechanism to bring the cam action pawls into and out of a locking engagement with the ratchet ring teeth so that the cam action pawls are engaged during the load-bearing phase of walking. Otherwise the teeth are disengaged.

DESCRIPTION OF THE INVENTION

It is not known in the art that multiple pawls permit a ratchet wheel to be locked when rotated a distance much shorter than the distance it must rotate when one pawl is used in a knee brace. Two pawls are disclosed in U.S. Pat. No. 4,520,804, but they are employed to enable the user to quickly and easily alter the relative pivotal movement and positioning between upper and lower leg sections. One pawl limits clockwise rotation, and one pawl limits counterclockwise rotation. The double locking ratchet knee joint in U.S. Pat. No. 4,520,804 accomplishes this movement through the use of manually actuatable locking levers. Thus, heretofore knee braces would not lock until the pawl moved a distance of at least one full tooth, during which the user's leg was unsupported. As will be appreciated, herein the pawl can be made to move less than the distance between two teeth. For a better understanding of how this is accomplished a description of the invention in conjunction with the accompanying drawings will be helpful.

THE INVENTION

Figure 1:
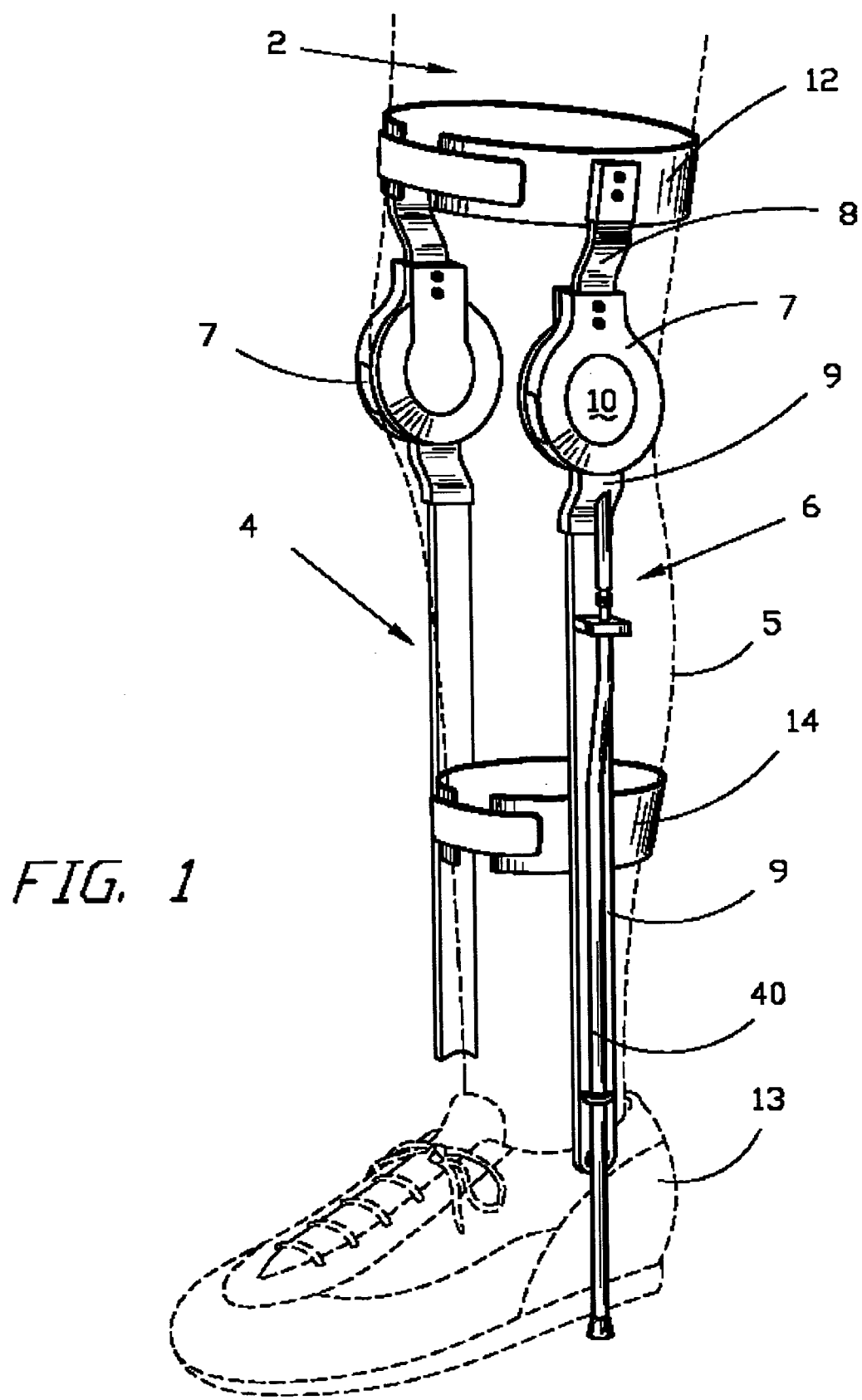
FIG. 1 is a perspective view showing the use of a knee brace constructed in accordance with this invention.

Referring now to these drawings, a knee brace 2 constructed in accordance with this invention is illustrated in FIG. 1. The brace resembles conventional knee braces having right and left supporting brace members 4 and 6 along with a knee joint assembly 7. The physiology of a knee brace requires that the brace on each side of the knee be different in orientation, but that each brace include identical knee joint assemblies. This being the case only the brace on one side of a leg, illustrated by reference character 6 herein, the left brace relative to the user, need be discussed in detail. In FIG. 1 it can be seen that left brace 6 includes an upper side brace 8, and a lower side brace 9 with housing 10 holding a mechanical pivotal knee joint assembly. To secure the knee brace to the leg 5, bands or straps 12 and 14 of flexible material such as fabric or leather are used with fasteners such as VELCRO® or snaps. One band 12 is wrapped around the upper leg to hold upper side brace 8 against that portion of the leg, and if the lower side brace 9 is not held firmly against the lower leg portion by a shoe 13 or an actuating mechanism such as a heel plate or an ankle flexure, a lower band 14 is used.

It is to be understood that the upper side brace 8 and lower side brace 9 should move relative to each other in a manner simulating, as closely as possible, ordinary leg movements. It is this relative movement that is the essence of this invention. In FIG. 1 it can be seen that since the upper leg must move from a bent leg position to a straight leg position, the upper side brace 8 must move relative to the lower side brace 9 as does a leg. To this end knee joint housing 10 is made up of two elements, an inner housing member and an outer housing member. Since the upper side brace must move as the leg is bent, upper side brace 8 is bolted or riveted, or otherwise rigidly connected, using holes 18 (FIG. 2) to outer housing member 19. Similarly lower side brace 9 is rigidly connected using holes 58 (also FIG. 2) to inner housing member 20, allowing the knee to flex when the user is not requiring support. These inner and outer housing members or elements, to be described in conjunction with the remaining figures, are coupled together to form a pivotal knee joint hinge in which the two housing members can rotate relative to each other.

Figures 2, 3:
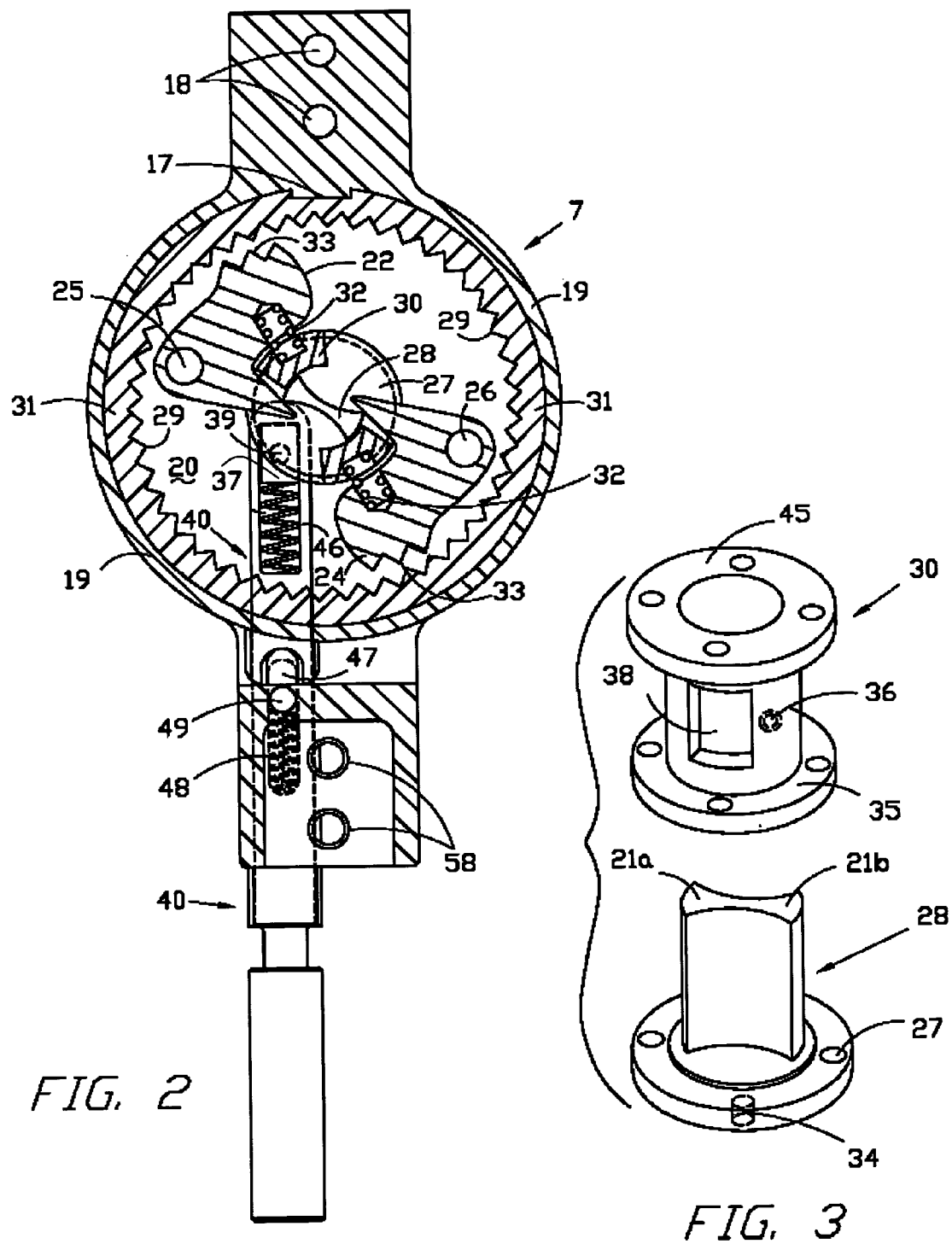
FIG. 2 is a cross sectional sketch illustrating a two pawl knee brace mechanism of the invention.
FIG. 3 is an isometric sketch showing the spool and shaft portions of the two pawl actuating mechanism.

Now that the invention has been described in general terms in conjunction with FIG. 1, it remains to describe it now more specifically in conjunction with FIG. 2. It has been emphasized that the key to such braces is the mechanical knee joint assembly within housing 10 illustrated in FIG. 1. FIG. 2 is a cross sectional diagrammatic view of one type of mechanism contemplated by this invention, and housed as a mechanical knee joint in housing 10. It can be seen that the upper side brace 8 is integral with the outer housing member 19, being keyed thereto at 18. Lower side brace 9 is joined to the inner housing member 20. A ratchet ring 31 having internal teeth 29 is mounted in the outer housing member 19 so that ratchet ring 31 rotates when the upper side brace 8 swivels. It has been indicated hereinbefore that a number of cam action pawls, with teeth adapted to engage the internal ratchet ring teeth, are mounted in the housing. They are mounted for operation around a central shaft or sleeve 30 which is joined to the inner housing member 20. Two such cam action pawls 22 and 24 are illustrated in FIG. 2. Cam action pawls 22 and 24 are spring pawls having teeth 33 which engage the teeth 29 in the ratchet ring. Cam action pawls 22 and 24 pivot about pins 25 and 26 in order to engage the teeth of the ratchet ring when the pawls are advanced by a spool 28 to be described subsequently. The pawls will then be held in place by the action of springs 32 which are seated in a sleeve or shaft 30, the shaft being a hollow cylinder surrounding and supporting rotating drive spool 28, as shown in FIG. 3, also to be described in greater detail.

On examining ratchet ring 31 and cam action pawls 22 and 24 it will be appreciated that means must be incorporated in the knee joint assembly to advance the cam action pawls so that one of them will lock the ratchet ring during use, and so that the pawl will be held in the locked position until weight is no longer supported by the brace. One such means is illustrated in FIG. 3.

FIG. 3 is an exploded isometric view of a shaft or sleeve 30 and a drive spool 28. Referring to FIG. 3 it can be seen that drive spool 28 is adapted to fit slidably within shaft 30. The shaft is a hollow cylinder provided with lower and upper flanges 35 and 45 respectively with holes for pins 25 and 26. The spool is a spindle having two lobes 21a and 21b which are adapted to advance cam action pawls 22 and 24. The outer portion of shaft 30 is provided with openings 38 through which tangs of the cam action pawls 22 and 24 project in order to be advanced by the lobes of the drive spool 28. Shaft 30 also provides seats 36 for pawl return springs 32, and the base 27 of drive spool 28 carries a recess 34 adapted to hold an actuator or cranking pin 39 as will be described.

It remains to return to FIG. 2 to describe the components of the actuating mechanism or pawl drive means 40 which operates the ratchet pivotal knee joint of this invention. This can best be accomplished by describing the operation of the leg brace. In order to prevent the user's knee from buckling or collapsing during walking, knee joint assembly 7 must lock when it is supporting a user's weight. To this end the knee joint assembly must be adapted to be locked by upward linear movement of an actuator rod 40 that is urged upwardly by the pressure of the walking surface upon the rod end, or by a heel plate or ankle flexure as in the prior art. Actuator rod 40 is also illustrated in FIG. 1. By this embodiment actuator rod 40 extends slightly below the shoe sole so that during use the weight of the walker forces it upwardly toward housing 10. This travel advances cam action pawls 22 and 24 by converting linear rod movement to angular spool movement so that drive spool 28 can advance the pawls. Herein this conversion is accomplished by a cranking action. As seen in FIG. 3 the base 27 of spool 28 is provided with a cavity 34 having a size and depth to receive a cranking pin 39 illustrated in FIG. 2. As can be understood from FIG. 2 as cranking pin 39 advances, spool 28 rotates slightly, say, twenty degrees, so that a return spring 32 can press teeth 33 of one of the pawls into engagement with ratchet teeth 29.

To permit actuator rod 40 to advance, due to the force of a user's weight, beyond the point of pawl engagement, cranking pin 39 is carried in a slide 37 which also carries spring 46. Slide 37 permits the actuator rod 40 to move beyond the pawl-locked position. At the same time spring 46 is compressed to hold drive spool 28 in position. To return actuating rod 40 to its lowered (no load) position a slot 47 is also incorporated in the actuator mechanism. Pin 49 is secured in inner housing 20 and passes through slot 47 allowing upper movement of the actuator rod, but with spring 48 returning the actuator rod to its downward no-load position when the knee brace 2 is not supporting weight.

PREFERRED EMBODIMENT OF THE INVENTION

Figure 4:
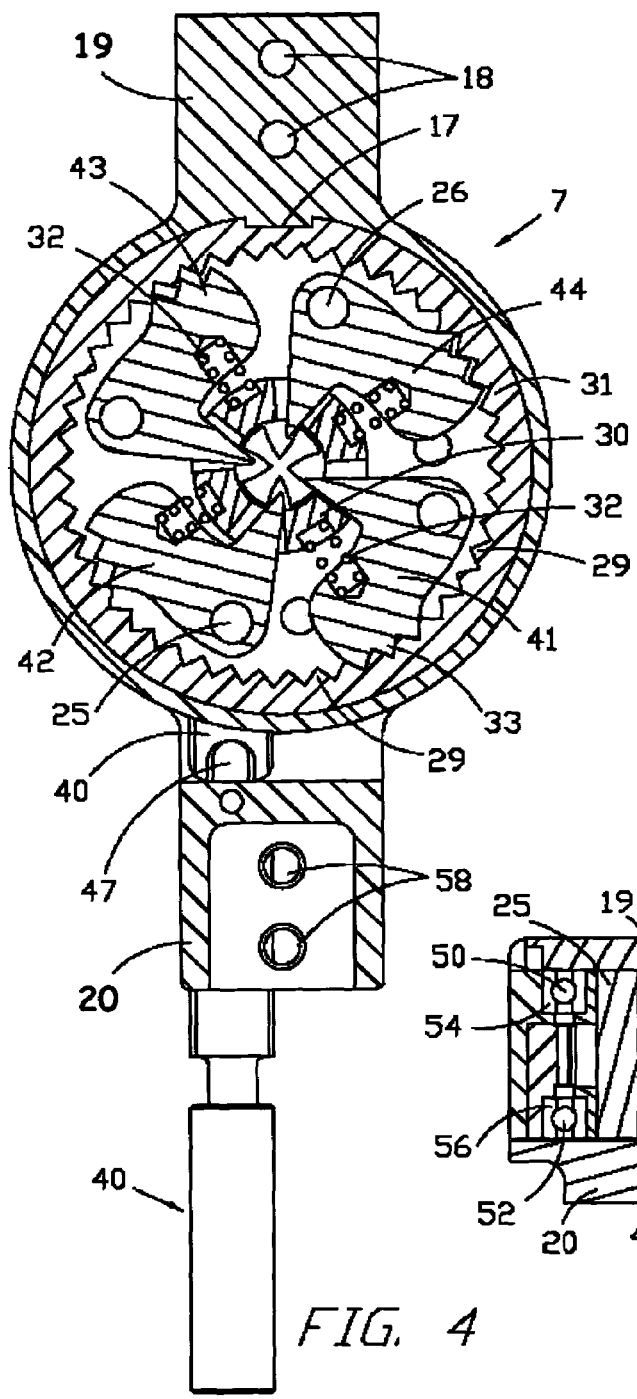
FIG. 4 is a cross sectional sketch illustrating a four pawl pivotal knee joint of the invention.

Referring now to FIG. 4, it is to be understood that the knee joint assembly shown in this figure is the same as that illustrated in FIG. 2 except that the pivotal knee joint hinge in FIG. 2 includes two cam action pawls mounted 180 degrees apart whereas the preferred knee joint assembly 7 of FIG. 4 includes four cam action pawls 41 through 44 mounted 90 degrees apart with only the teeth 33 of cam action pawl 41 in engagement with teeth 29 of ratchet ring 31. It is noted that upper brace 8, lower brace 9, actuator rod 40, and slide 37 (not shown) and slot 47 are the same components operating in the same manner as the components described in conjunction with FIG. 2. Since actuator 40 is identical in operation to that described in connection with FIG. 2, it is considered unnecessary to cut away FIG. 4, as was done in FIG. 2, and to repeat the actuation description.

A particularly novel feature of this invention is that when teeth 33 and 29 are locked together so that the user's knee joint will not bend, knee joint assembly 7 permits the bent knee to be straightened. As can be visualized, springs 32, along with the design of the pawl teeth, lock the knee joint assembly against movement in the knee bending direction (counterclockwise in FIG. 4), but permit movement in the knee straightening direction. An examination of the slopes of teeth 33 and 29 confirm that ratchet ring 31 can be rotated in a clockwise direction, in this instance the knee straightening direction.

Figure 5:
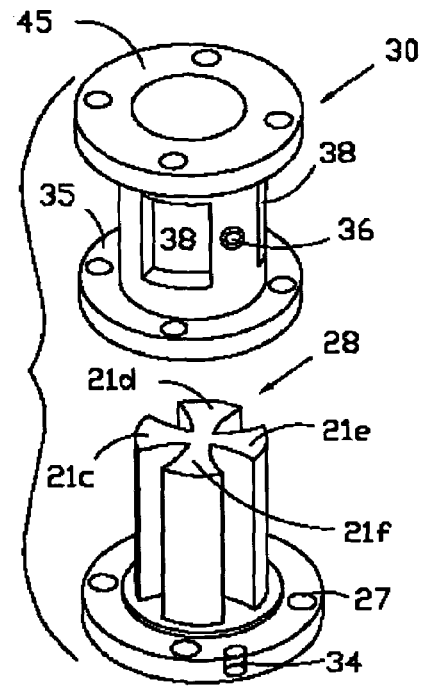
FIG. 5 is an isometric sketch showing the spool and shaft portions of the four pawl knee brace mechanism.

FIG. 5 is an exploded isometric view of a shaft 30 and drive spool 28 resembling that of FIG. 3 with drive spool 28 again being adapted to fit slidably within shaft 30. As in the embodiment in FIG. 3 the shaft is a hollow cylinder provided with lower and upper flanges 35 and 45 respectively. In this instance the flanges have four holes for the cam pawl pins. As in the FIG. 3 embodiment the spool is also a spindle, but one having a different configuration in order to accommodate four pawls. Thus drive spool 28 is provided with four lobes 21c, 21d, 21e, and 21f. The outer portion of shaft 30 in this embodiment is provided with four openings 38 through which the four tangs of the four cam action pawls 41, 42, 43 and 44 project in order to be advanced by lobes of the drive spool 28. Shaft 30 also provides seats 36 for pawl return springs 32, and the base 27 of drive spool 28 carries a recess 34 holding the actuator pin as described hereinbefore.

The more closely a knee joint assembly is to simulate the functioning of a human knee, the smaller the increments between joint locking positions should be. The main thrust of this invention is the discovery that increment size is a function of the number of cam action pawls in the knee joint assembly. The function can be determined when the number of internal ratchet ring teeth are brought into the equation. Considering the invention herein, there are 45 teeth on the ratchet ring. With the ratchet ring being a circle, dividing 45 into 360 degrees reveals that the teeth herein are 8 degrees apart. The 4 pawls in the embodiment illustrated in FIG. 4 are mounted 90 degrees apart. With the teeth being 8 degrees apart, there are 90/8, or 11.25 teeth in each quadrant. Hence when one pawl is fully engaged, the next pawl is 0.25 tooth distance (a fourth of the distance between two teeth) from engagement. In other words, considering the 8 degree ratchet teeth separation, a 2 degree rotation will cause the next pawl in FIG. 4 to lock the leg brace. Likewise, in the 2 pawl pivotal knee joint hinge illustrated in FIG. 2, with the pawls being 180 degrees apart, and the teeth being 8 degrees apart, there are 180/8 or 22.5 teeth in each quadrant. In this instance a spool rotation of one-half of the distance between two teeth will cause the next pawl to engage.

Figure 6:
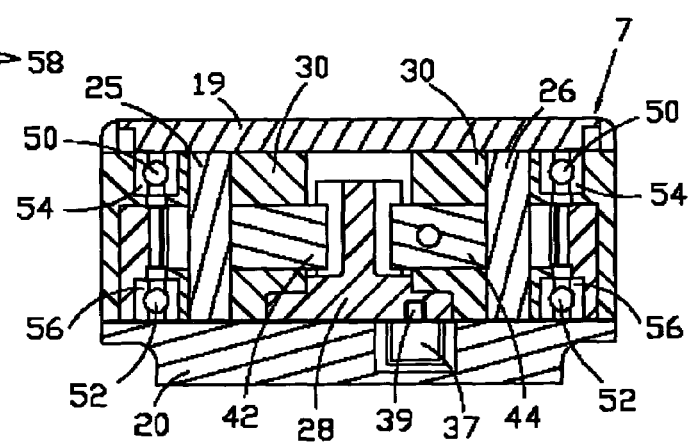
FIG. 6 is a cross sectional diagrammatic view of the four pawl pivotal knee joint hinge of FIG. 4.

It can be seen that by the practice of this invention the knee joint assembly locks with the upper brace moving extremely small distances, for instance two or four degrees, thus securing the knee joint in virtually any position to prevent the knee from collapsing. In addition, when actuated, the knee brace will positively lock in one direction while allowing rotation in the other direction. When not actuated, the knee brace will allow rotation in both directions. Further, the actuation means herein does not require that the mechanism be a part of a shoe or stirrup. Hence given the teachings of this invention ramifications and variations will occur to those skilled in the art. For example a protective tip, such as the rubber tip shown in FIG. 1, can be secured to the tip of the actuation rod. As another example bearings can be incorporated in the knee joint assembly of the invention so that outer and inner housing members 19 and 20 will be able to move more readily with respect to each other. The use of such bearings is illustrated in FIG. 6. This figure is a cross sectional view of the knee joint assembly of the invention showing pawls 42 and 44, along with their pins 25 and 26. Also shown are shaft 30, drive spool 28 and spool cranking pin 39. Bearings 50 and 52 are shown in FIG. 6 in their respective races 54 and 56, positioned between outer and inner housing members 19 and 20. As another variation it will occur to one skilled in the art that the pawls need not have three locking teeth, but one or more can be utilized depending upon the calculation which determines the number and material necessary to support the load. Likewise the number of pawls rendering smaller and smaller locking increments will be determined by the sizes of the components. Such modifications, then, are deemed to be within the scope of this invention.

What is claimed is:

1. An orthopedic knee brace mechanism incorporating upper and lower side braces adapted to support a portion of a user's leg above and below the user's knee with a knee joint housing there between adapted for pivotal movement, and leg bands adapted to secure the side braces against the user's leg, the knee joint housing comprising inner and outer housing members, the upper side brace being integral with the outer housing member so as to move therewith, and the lower side brace being integral with the inner housing member so as to move with it, a ratchet ring having internal teeth, the ratchet ring being mounted in the outer housing member so as to rotate when the upper side brace swivels, a plurality of cam action pawls mounted for operation around a central shaft in the inner housing member, the pawls being provided with teeth adapted to engage the internal ratchet ring teeth, and also with return springs to hold the pawl teeth in engagement with the ratchet ring teeth when they are engaged, means for coupling the inner and outer housing members to form a knee joint hinge in which the cam action pawls in the inner housing member engage the teeth inside the ratchet ring in the outer housing member, forming a ratchet within the housing, a control mechanism within the housing adapted to move the pawls into and out of a locking engagement with the ratchet ring teeth, the cam action return springs and the shape of the cam action pawl teeth being adapted so that the pawls allow rotation of the ratchet ring in a leg straightening direction while still supporting a load so that the leg can be extended for walking while at the same time being prevented by the cam action pawls from buckling in the knee bending direction, and an actuating rod adapted to drive the control mechanism to bring the cam action pawls into and out of a locking engagement with the ratchet ring teeth, advancing the cam action pawls when the user's foot engages a walking surface and disengaging the cam action pawls when the user's foot is not in the load bearing phase of walking.

2. The orthopedic knee brace mechanism of claim 1 wherein four cam action pawls are mounted for operation around the central shaft in the inner housing member, wherein the control mechanism within the housing is a star shaped cam spool mounted for rotation in the central shaft, the cam spool having four points adapted on forward or rearward rotation to engage and disengage the cam action pawls, and wherein the actuating rod supports a crank pin extending into a hole eccentrically positioned in the bottom of the cam spool, and spring means enabling the crank pin to move the cam action pawls into engagement and disengagement with the ratchet ring internal teeth.

3. The orthopedic knee brace mechanism of claim 1 wherein two cam action pawls are mounted for operation around the central shaft in the inner housing member, wherein the control mechanism within the housing is a spindle shaped cam spool mounted for rotation in the central shaft, the cam spool having two points adapted on forward or rearward rotation to engage and disengage the cam action pawls, and wherein the actuating rod supports a crank pin extending into a hole eccentrically positioned in the bottom of the cam spool, and spring means enabling the crank pin to move the cam action pawls into engagement and disengagement with the ratchet ring internal teeth.

4. A pivotal knee joint hinge for inclusion in a knee joint housing between upper and lower side braces of an orthopedic knee brace mechanism, the pivotal knee joint hinge including a ratchet ring mounted in the knee joint housing and adapted to rotate when the upper side brace swivels, the ratchet ring being provided with a plurality of internal teeth, at least two cam action pawls so mounted in the housing that they are able to engage the teeth inside the ratchet ring during use, a control mechanism within the housing adapted to advance the cam action pawls so that during use one of the cam action pawls is able to engage the ratchet ring teeth to hold the ratchet ring in a locked position in a knee bending direction to prevent a user's knee from buckling, the slopes of the ratchet rings internal teeth being such that the ratchet ring can be rotated out of the locked position by movement of the side brace in a knee straightening direction while at the same time allowing a second cam action pawl to engage teeth of the ratchet ring, thus decreasing to increments the distance the ratchet ring moves between locking positions by cam action pawls moving into, and out of, locking engagement with the ratchet ring internal teeth, the size of the increments being a function of the number of cam action pawls, and the number of internal ratchet ring teeth, and an actuating mechanism adapted to actuate the control mechanism to advance the pawls when the users foot presses on a walking surface, and to disengage the pawls when the users foot does not press on a walking surface.

* * * * *